United States Patent [19]

Hon et al.

[11] Patent Number: 4,947,865
[45] Date of Patent: Aug. 14, 1990

[54] SENSOR SUPPORT PLATE WITH DETACHABLE RING

[75] Inventors: Edward H. Hon, Bradbury; Edward D. Hon, San Francisco; Robert W. Hon, Los Altos, all of Calif.

[73] Assignee: The Hon Group, Encino, Calif.

[21] Appl. No.: 258,554

[22] Filed: Oct. 17, 1988

Related U.S. Application Data

[63] Continuation-in-part of Ser. No. 118,441, Nov. 9, 1987, which is a continuation-in-part of Ser. No. 915,120, Oct. 2, 1986, which is a continuation-in-part of Ser. No. 780,398, Sep. 26, 1985, abandoned, and a continuation-in-part of Ser. No. 858,713, May 2, 1986, abandoned, and a continuation-in-part of Ser. No. 163,859, Mar. 3, 1988.

[51] Int. Cl.$^5$ .............................................. A61B 5/103
[52] U.S. Cl. ..................................... 128/778; 128/775
[58] Field of Search ................................ 128/639-640, 128/774-775, 778, 780, 782, 798, 802-803, 662.04, 641, 672, 691, 662.03

[56] References Cited

U.S. PATENT DOCUMENTS

| | | | |
|---|---|---|---|
| 3,824,988 | 7/1974 | Soldner et al. | 128/662.04 |
| 3,859,984 | 1/1975 | Langley | 128/662.04 |
| 4,355,643 | 10/1982 | Laughlin et al. | 128/662.04 |
| 4,401,125 | 8/1983 | Taylor et al. | 128/639 X |
| 4,556,066 | 12/1985 | Semrow | 128/639 X |

Primary Examiner—Angela D. Sykes
Attorney, Agent, or Firm—Lewis Anten

[57] ABSTRACT

A sensor support base having a rigid inner portion and a relatively flexible outer ring portion removably attached around its periphery for adhesive application to a patient is disclosed. The relatively flexible outer ring portion has a relatively rigid segment for assisting in attachment to the periphery of the inner portion. A layer of absorbent material on the upper surface of the outer ring portion is used for absorbing perspiration of the patient.

28 Claims, 1 Drawing Sheet

SENSOR SUPPORT PLATE WITH DETACHABLE RING

RELATED APPLICATIONS

This is a continuation-in-part of patent application entitled "Improved Sensor Support Base and Method of Application", Ser. No. 118,441, Nov. 9, 1987, pending which is a continuation-in-part of patent application entitled External Uterine Contraction Monitoring Device, Ser. No. 915,120, filed by Edward H. Hon, M.D., Edward D. Hon and Robert W. Hon, on Oct. 2, 1986, pending which was a continuation-in-part of patent application Continuous Cutaneous Blood Pressure Measuring Apparatus and Method, Ser. No. 780,398, filed by Edward H. Hon, M.D. and Edward D. Hon, on Sept. 26, 1985, now abandoned and a continuation-in-part of patent application entitled Apparatus for Measuring Blood Pressure, Ser. No. 858,713, filed by Edward H. Hon, M.D. and Edward D. Hon, on May 2, 1986, now abandoned and a continuation-in-part of patent application entitled "Improved Transducer Support Base with a Depending Annular Ring", Ser. No. 163,859, filed on Mar. 3, 1988.

BACKGROUND OF THE INVENTION

In the co-pending application entitled "Improved Sensor Support Base and Method of Application", Ser. No. 118,441 a support base for a monitoring device for monitoring the contractions of a patient in labor was disclosed. The apparatus consisted of a concave support base having a central relatively rigid transducer holding member and a relatively flexible outer ring portion.

OBJECTS OF THE PRESENT INVENTION

It is an object of the present invention to provide a support base that is easy to manufacture.

It is another object of the present invention to provide a support base which provides easier alignment of the outer ring portion to the inner portion.

It is another object of the present invention to provide an improved support base which is less likely to come off during use.

It is another object of the present invention to provide a support plate that may be more easily and more inexpensively made.

These and other objects of the present invention will be evident from a review of the specification and the accompanying drawings.

SUMMARY OF THE INVENTION

In the present invention the improved support base is designed to be adhesively applied to the abdomen of the patient. It is substantially concave and consists of a first inner portion having an opening for receiving a transducer. The inner portion is relatively rigid in relationship to a second relatively flexible outer ring portion which extends substantially around the periphery of the inner portion of the support base. In the preferred embodiment the support base is circular.

The first relatively rigid inner portion is made of hard plastic, while the second relatively flexible outer ring portion is made of a relatively soft material, such as plastic or rubber material. This permits the support base to fit a wide range of abdominal sizes from the relatively small to the very large. Also, the flexible outer ring portion, due to its flexibility, may be more easily removed from the patient after use.

The outer flexible outer ring portion has a relatively rigid central portion which is force fit over a ridge on the periphery of the inner portion. In the preferred embodiment, an absorbent material overlays a portion of the top of the relatively flexible outer ring portion, and an absorbent sponge material is located on the bottom surface of the inner portion, substantially surrounding the opening in the inner portion.

Further details of the invention will be evident from a review of the following descriptions of the drawings and the detailed description of the invention.

DETAILED DESCRIPTION OF THE INVENTION

Figure 1:
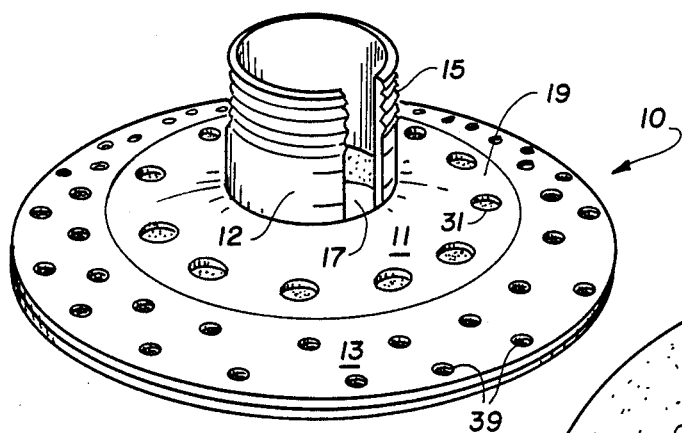
FIG. 1 is a top perspective view of the present invention.
Figure 3:
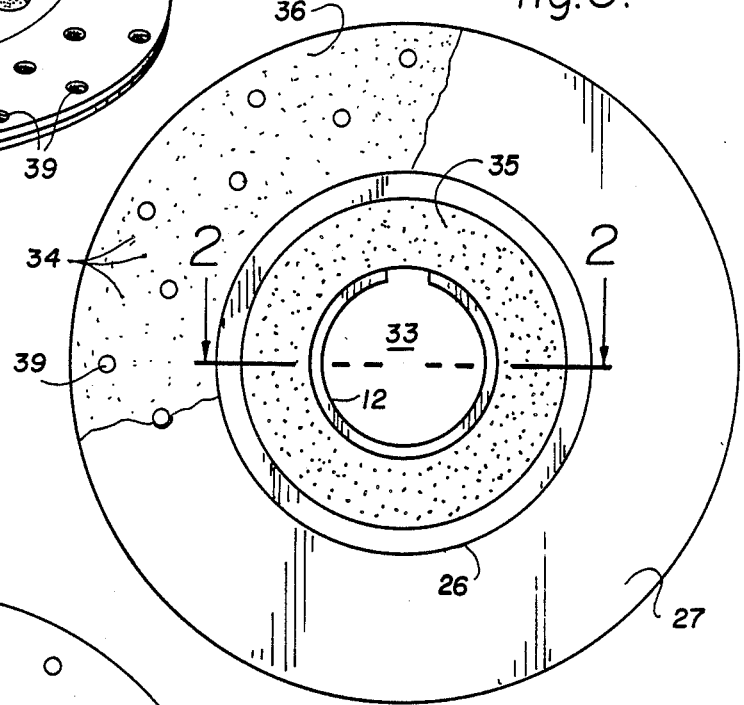
FIG. 3 is a bottom view of the support base of FIG. 1.
Figure 4:
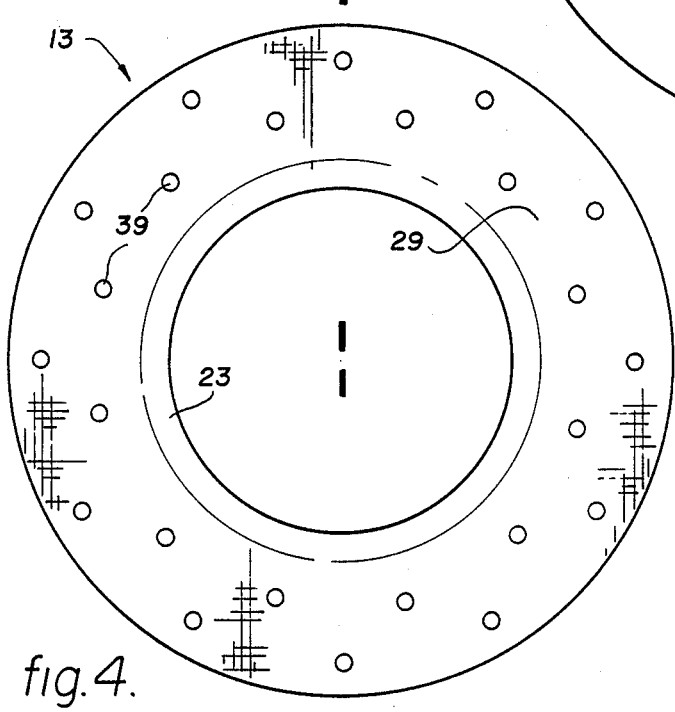
FIG. 4 is a top view of the outer relatively flexible ring.
Figure 2:
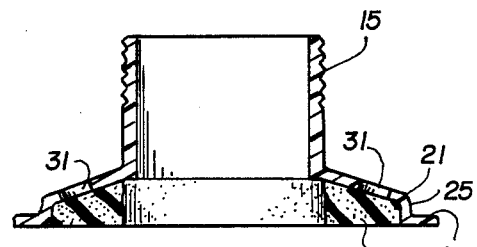
FIG. 2 is a side sectioned view of the inner rigid portion of the support base taken along section lines 2—2 of FIG. 3.
Figure 5:
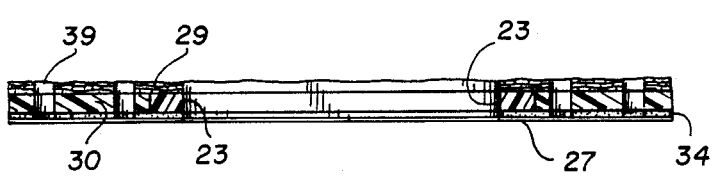
FIG. 5 is a side sectional view of the outer ring taken along lines 5—5 of FIG. 4.

Making reference to FIGS. 1–5, a substantially concave support base 10 comprising an relatively rigid inner portion 11 and a flexible outer ring portion 13 is shown. An upstanding hollow tubular member 12 is mounted perpendicular substantially at the center of the inner portion 11.

The hollow tubular member 12 may be formed integrally with the inner portion 11 of the support base 10 or removably attached by other means, such as by threads, force fitting or other coupling means. The tubular member 12 is threaded 15 at its upper end and has an internal diameter of approximately 1 inch.

Slot 17 in the tubular member 12 is adapted to permit electrical connections to pass through the wall of the tubular member 12. The upper portion of the hollow tubular member extends approximately 1 ½ inches above the top surface 19 of the inner portion 11.

The inner portion 11, in the preferred embodiment, is circular and the outside diameter of the inner portion 11 is approximately 3 inches. The inner portion 11 is made of a relatively rigid plastic material and the outer relatively flexible portion 13 is made of a soft flexible rubber or plastic material. The support base 10 has an outer diameter large enough to provide a sufficient surface area in contact with the skin of the patient to withstand vertical lifting of the sensor support plate. It has been found that an outside diameter of approximately 5 inches for the outer ring portion is highly acceptable. The first inner portion 11 has a thickness of about ⅛ inch.

The outer ring portion 13 has a relatively rigid central ring 23 at the periphery of the inner opening which is approximately ¼ inch in width and ⅛ inch thick. The central ring 23 fits over the ridge 21, and force fits against the shoulder 25 of the ridge 21, resting on flange 26. The rigid ring is made of plastic.

In an alternative embodiment the outer ring portion may be made so as to have a thickened portion at its inner portion for directly force fitting over the ridge 21.

While in the preferred embodiment the outer ring is attached by a force fit, other means of attachment, such as threads, clamps, adhesive, or other means may be employed.

The outer ring portion surrounding the relatively rigid central ring 23 is a relatively flexible plastic or rubber member 30. An adhesive layer 34 covers its lower surface which is in turn covered by an easily removable wax paper backing 27 conventionally used in medical adhesive devices. The top surface of the outer ring portion 13 is covered by an absorbent material 29 having small openings 39 that pass through the flexible plastic or rubber portion 30.

The adhesive 24 is of a medical grade and is applied to the bottom 36 surface of the support base by conventional means. This may be sprayed on or applied by use of a double sided adhesive.

A series of openings 31 are formed in the inner portion 11 to permit the skin to "breathe" and also to permit a solvent solution to pass through the openings to dissolve the adhesive so as to facilitate removal of the support plate from the skin.

A flexible membrane, not shown, may be provided to cover the opening 33 so that any transducer in the opening 33 is maintained away from physical contact with the patient.

It has been found that during labor body perspiration can cause the adhesive contact with the skin to be loosened. To prevent the perspiration from loosening the adhesive, a highly absorbent sponge material 35 is applied to the bottom surface 16 of the inner portion 11 surrounding the opening 33. The highly absorbent materials, may be paper, such as used in breast shields, disposable diapers and cotton napkins, sponges, or fabrics, such as cotton.

The highly absorbent materials serve to prevent perspiration from coming into contact with the adhesive in the vicinity of the perimeter of the support base, reducing the likelihood that the support base will accidentally lift from the patient. The absorbent material 29 and 35 also permit the evaporation of the perspiration through the openings 39 and 31.

While in the preferred embodiment the inner portion 11 is plastic, it could be made out of water absorbent materials that hold their shape, such as pressed cardboard or paper mache. Such materials can be easily and inexpensively manufactured and would hold their shape for substantial periods of time, just like a paper plate. In such a case, the absorbent sponge 35 would be unnecessary.

In operation, the skin of the patient is cleansed with alcohol and then swabbed with a quick drying solution e.g., collodion to provide a uniform base for the adhesive as well as a readily dissolvable layer which permits easy removal of the sensor support base at the termination of the procedure.

Once the patient is prepared, the outer ring portion 13 is fitted over the inner portion 11 and the paper backing 27 is removed from the outer ring portion. The support base is then attached to the abdomen of the patient. The support base is maintained in contact with the patient until it is desired to remove it. This is accomplished by applying a solvent, such as alcohol, through the openings 31 and 39 to the area. This can be done by spray or cloth. It has been found to be particularly advantageous to apply the solution around the periphery of the support base while gently lifting the periphery of the flexible outer ring portion 13 of the support base 10. The outer ring portion 13 can then be removed from the inner portion 11 and disposed of or the entire support plate 10 can be thrown away.

It is recognized that the absorbent material 35 and 29 may not be required on all contraction support plates, but it may be desirable, due to the additional cost, to employ such configuration only for those patients in those climatic conditions where it is believed that it will be necessary. It has been found that most patients do not require this feature. Also, while the apparatus has been described in association with use on the abdomen of a patient for recording contractions, the claimed invention may be readily adapted for use in the recording of other data, used at other locations of the patient, such as respiration.

While the present invention has been described with regards to the preferred embodiment, it is recognized that other variation of the present invention can be made without departing from the inventive concept described herein.

What is claimed is:

1. A sensor support comprising a support base, having: an opening therein, for supporting a transducer sensor and support base having a relatively rigid inner portion with an opening therethrough such that a transducer can be reversibly passed through the base, and a relatively flexible outer ring portion non integral with the inner portion and which is removably attached to at least a portion of the periphery of said relatively rigid inner portion.

2. The sensor support of claim 1 in which said outer ring portion comprises soft flexible rubber.

3. The sensor support of claim 1 in which said outer ring portion comprises soft flexible plastic.

4. The sensor support of claim 1 in which said inner portion comprises a relatively rigid plastic.

5. The sensor support of claim 1 in which said inner portion comprises a paper product.

6. The sensor support of claim 5 in which said inner portion comprises cardboard.

7. The sensor support of claim 1 in which said outer ring portion is relatively rigid at the portion surrounding the periphery of said inner portion.

8. The sensor support of claim 7 in which said rigid portion of said outer ring portion extends substantially around the entire periphery of said inner portion.

9. The sensor support of claim 7 in which said outer ring portion has adhesive means attached to its lower surface.

10. The sensor support of claim 1 in which a flexible membrane covers said opening in said support base.

11. A sensor support comprising a support base including means for supporting a transducer sensor, said support base having an opening therethrough, such that a transducer can be reversibly passed, an upper and lower surface and a moisture absorbent material on at least a portion of the upper surface of said support base.

12. A flexible flat adhesive ring member comprising a thin layer of a relatively flexible material, having an upper surface and a lower surface, said ring member having a central opening and a relatively rigid material substantially surrounding said opening, said flexible material having adhesive applied to said lower surface.

13. The adhesive ring of claim 12 in which said flexible material is formed integrally with said relatively rigid material.

14. A sensor support comprising a support base, including means for supporting a transducer sensor, said support base having an opening therethrough, an upper and a lower surface and a moisture absorbent material on at least a portion of the upper surface of said support base, and including absorbent material on the lower surface surrounding said opening in the support base.

15. The sensor support of claim 14 in which said absorbent material is an absorbent paper.

16. The sensor support of claim 14 in which said absorbent material is sponge.

17. A flexible flat adhesive ring member comprising a thin layer of a relatively flexible material, having an upper surface and a lower surface and said ring member having a central opening and a relatively rigid material substantially surrounding said opening, said flexible material having adhesive applied to said lower surface and absorbent material on at least a portion of the upper surface of said ring member.

18. The ring member of claim 17 in which said absorbent material is an absorbent fabric.

19. The ring of claim 17 in which said flexible material has openings there through.

20. The ring of claim 17 in which said absorbent material is absorbent paper.

21. The ring of claim 17 in which said absorbent material is sponge.

22. A sensor support comprising a support base having an opening therein for supporting a transducer sensor, said support base having an upper and a lower surface and an absorbent material on a portion of the lower surface.

23. The sensor support of claim 22 wherein said support base has a relatively rigid inner portion which has the opening for supporting a transducer sensor, and has a relatively flexible outer portion.

24. The sensor support of claim 23 wherein at least a portion of the lower surface of said outer portion has adhesive means attached thereto.

25. The sensor support of any one of claims 22 to 24, additionally comprising an upwardly extending hollow tubular member communicating with the opening for supporting a transducer sensor.

26. A method of monitoring labor contractions using the sensor support of any one of claims 1, 14, or 22, comprising adhesively attaching the support base of the sensor support to the abdomen of a patient and passing a pressure transducer through the opening so that it can sense contractions of the patient's abdomen.

27. A flexible flat adhesive ring member comprising a thin layer of a relatively flexible material, having an upper surface and a lower surface, said ring member having a central opening and a relatively rigid portion substantially surrounding said opening, said flexible material having adhesive applied to said lower surface.

28. A sensor support comprising a support base having: a relatively rigid inner portion with an opening therethrough; and a relatively flexible outer ring portion non-integral with the inner portion and which is removably attached to at least a portion of the periphery of said relatively rigid inner portion, said sensor support further comprising a pressure transducer positioned within the opening in the inner portion and reversibly movable therethrough.

* * * * *